US012596115B2

(12) United States Patent
Neumann et al.

(10) Patent No.: US 12,596,115 B2
(45) Date of Patent: Apr. 7, 2026

(54) SYSTEMS AND METHODS FOR CAPACITOR ACTIVATION OF CONCRETE SENSORS

(71) Applicant: Hilti Aktiengesellschaft, Schaan (LI)

(72) Inventors: Jens Neumann, Grabs (CH); Ryan Twomey, Dedham, MA (US); Katelyn Jobes, Waltham, MA (US); Patrick Haldner, Schaan (LI)

(73) Assignee: Hilti Aktiengesellschaft, Schaan (LI)

( * ) Notice: Subject to any disclaimer, the term of this patent is extended or adjusted under 35 U.S.C. 154(b) by 82 days.

(21) Appl. No.: 18/389,956

(22) Filed: Dec. 20, 2023

(65) Prior Publication Data

US 2024/0210378 A1      Jun. 27, 2024

Related U.S. Application Data

(60) Provisional application No. 63/476,962, filed on Dec. 23, 2022.

(51) Int. Cl.
| | |
|---|---|
| *G01N 33/38* | (2006.01) |
| *G01D 11/00* | (2006.01) |

(Continued)

(52) U.S. Cl.
CPC ......... *G01N 33/383* (2013.01); *H04L 67/125* (2013.01)

(58) Field of Classification Search
CPC .... G01N 33/38; G01N 33/383; H04L 67/125; G01D 11/00; G01D 21/02; G06F 3/01; G06F 3/0346
See application file for complete search history.

(56) References Cited

U.S. PATENT DOCUMENTS

| | | |
|---|---|---|
| 10,386,210 B2 | 8/2019 | Dowdall et al. |
| 10,526,884 B2 * | 1/2020 | Babakhani .............. G01V 1/46 |

(Continued)

FOREIGN PATENT DOCUMENTS

| | | |
|---|---|---|
| CN | 203149799 U | 8/2013 |
| WO | 2017/100293 | 6/2017 |

(Continued)

OTHER PUBLICATIONS

Neumann et al., U.S. Appl. No. 63/476,958, filed Dec. 23, 2022.

(Continued)

*Primary Examiner* — Neel D Shah
(74) *Attorney, Agent, or Firm* — Grüneberg Global IP, PLLC

(57) ABSTRACT

A system includes a sensor device for monitoring properties of a building material within which the sensor device can be embedded. The sensor device has a controller, a memory associated with the controller, one or more sensors communicatively connected to the controller for measuring one or more properties of the building material, and a power supply for powering components of the sensor device. The power supply includes a capacitor and a power regulator. The sensor device includes a power management subcircuit for activating the power regulator for powering "ON" components of the sensor device via the capacitor, wherein the power management subcircuit receives an activation signal from an external power source to activate the sensor device, and wherein the external power source is configured to charge the capacitor.

8 Claims, 6 Drawing Sheets

(51) Int. Cl.
    *G01D 21/02*     (2006.01)
    *G06F 3/01*     (2006.01)
    *G06F 3/0346*     (2013.01)
    *H04L 67/125*     (2022.01)

(56)         References Cited

U.S. PATENT DOCUMENTS

| | | | |
|---|---|---|---|
| 2002/0057097 A1 | 5/2002 | Kelly et al. | |
| 2014/0216143 A1 | 8/2014 | Salmi et al. | |
| 2017/0160111 A1 | 6/2017 | Dowdall et al. | |
| 2019/0323865 A1 | 10/2019 | Dowdall et al. | |
| 2021/0063336 A1 | 3/2021 | Ghods et al. | |
| 2021/0166956 A1* | 6/2021 | Tatsumi | C23C 14/564 |
| 2021/0321240 A1 | 10/2021 | Reisbick | |
| 2022/0034724 A1 | 2/2022 | Cathcart et al. | |
| 2022/0107251 A1 | 4/2022 | Ghods et al. | |
| 2023/0047417 A1 | 2/2023 | Gordi | |
| 2025/0164413 A1 | 5/2025 | Ghods et al. | |

FOREIGN PATENT DOCUMENTS

| | | |
|---|---|---|
| WO | 2020/210861 | 10/2020 |
| WO | 2024/132700 | 6/2024 |

OTHER PUBLICATIONS

Neumann et al., U.S. Appl. No. 63/476,959, filed Dec. 23, 2022.
Neumann et al., U.S. Appl. No. 63/476,960, filed Dec. 23, 2022.
Neumann et al., U.S. Appl. No. 63/476,961, filed Dec. 23, 2022.
Neumann et al., U.S. Appl. No. 63/476,962, filed Dec. 23, 2022.
Neumann et al., U.S. Appl. No. 18/390,054, filed Dec. 20, 2023.
Neumann et al., U.S. Appl. No. 18/390,282, filed Dec. 20, 2023.
Neumann et al., U.S. Appl. No. 18/390,387, filed Dec. 20, 2023.
U.S. Appl. No. 63/476,958, filed Dec. 23, 2022, Neumann et al.
U.S. Appl. No. 63/476,959, filed Dec. 23, 2022, Neumann et al.
U.S. Appl. No. 63/476,960, filed Dec. 23, 2022, Neumann et al.
U.S. Appl. No. 63/476,961, filed Dec. 23, 2022, Neumann et al.
U.S. Appl. No. 63/476,962, filed Dec. 23, 2022, Neumann et al.
U.S. Appl. No. 18/390,054, filed Dec. 20, 2023, Neumann et al.
U.S. Appl. No. 18/390,282, filed Dec. 20, 2023, Neumann et al.
U.S. Appl. No. 18/390,387, filed Dec. 20, 2023, Neumann et al.

* cited by examiner

SYSTEMS AND METHODS FOR CAPACITOR ACTIVATION OF CONCRETE SENSORS

CROSS-REFERENCE TO RELATED APPLICATIONS

This application claims priority to U.S. Application No. 63/476,962 filed on Dec. 23, 2022, the content of which is hereby incorporated by reference in its entirety.

BACKGROUND OF THE INVENTION

Field of the Invention

The present disclosure relates generally to the field of building structures, and more particularly to systems and methods for capacitor activation of sensors utilized for monitoring properties of concrete slabs in building structures.

Description of Related Art

Within building structures, various types of sensors may be utilized to monitor one or more properties of building materials, such as concrete slabs or epoxy. For example, one or more concrete sensors may be embedded into a building structure to monitor one or more properties of the building material. In certain situations, the properties of the building material being monitored may include, for example, strength, humidity, temperature, vibration, pH, gas and particle presence, load, acoustic properties, or any other physical property that provides an indication of the health of the building material. The concrete sensors embedded into the building structure may collect and send sensor data wirelessly to a remote computing device, such as a smartphone, tablet, gateway, or other computer device operated by users outside of the building structure.

In certain situations, these sensors may be light activated after removing the sensor from light blocking packaging. However, it may be beneficial to provide for other methods of sensor activation so that a user may have greater flexibility and ease of installation. Accordingly, it may be beneficial to provide systems and methods for capacitor activation of sensors utilized for monitoring properties of building materials (e.g., concrete, epoxy, etc.) in building structures.

SUMMARY OF THE INVENTION

Certain embodiments commensurate in scope with the originally described subject matter are summarized below. These embodiments are not intended to limit the scope of the described subject matter, but rather these embodiments are intended only to provide a brief summary of possible forms of the subject matter. Indeed, the subject matter may encompass a variety of forms that may be similar to or different from the embodiments set forth below.

In a first embodiment, a system includes a sensor device for monitoring properties of a building material within which the sensor device can be embedded. The sensor device a controller, a memory associated with the controller, one or more sensors communicatively connected to the controller for measuring one or more properties of the building material, and a power supply for powering components of the sensor device. The power supply comprises a capacitor and a power regulator. The sensor device includes a power management subcircuit for activating the power regulator for powering "ON" components of the sensor device via the capacitor, wherein the power management subcircuit receives an activation signal from an external power source to activate the sensor device, and wherein the external power source is configured to charge the capacitor.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION OF THE INVENTION

Figure 1:
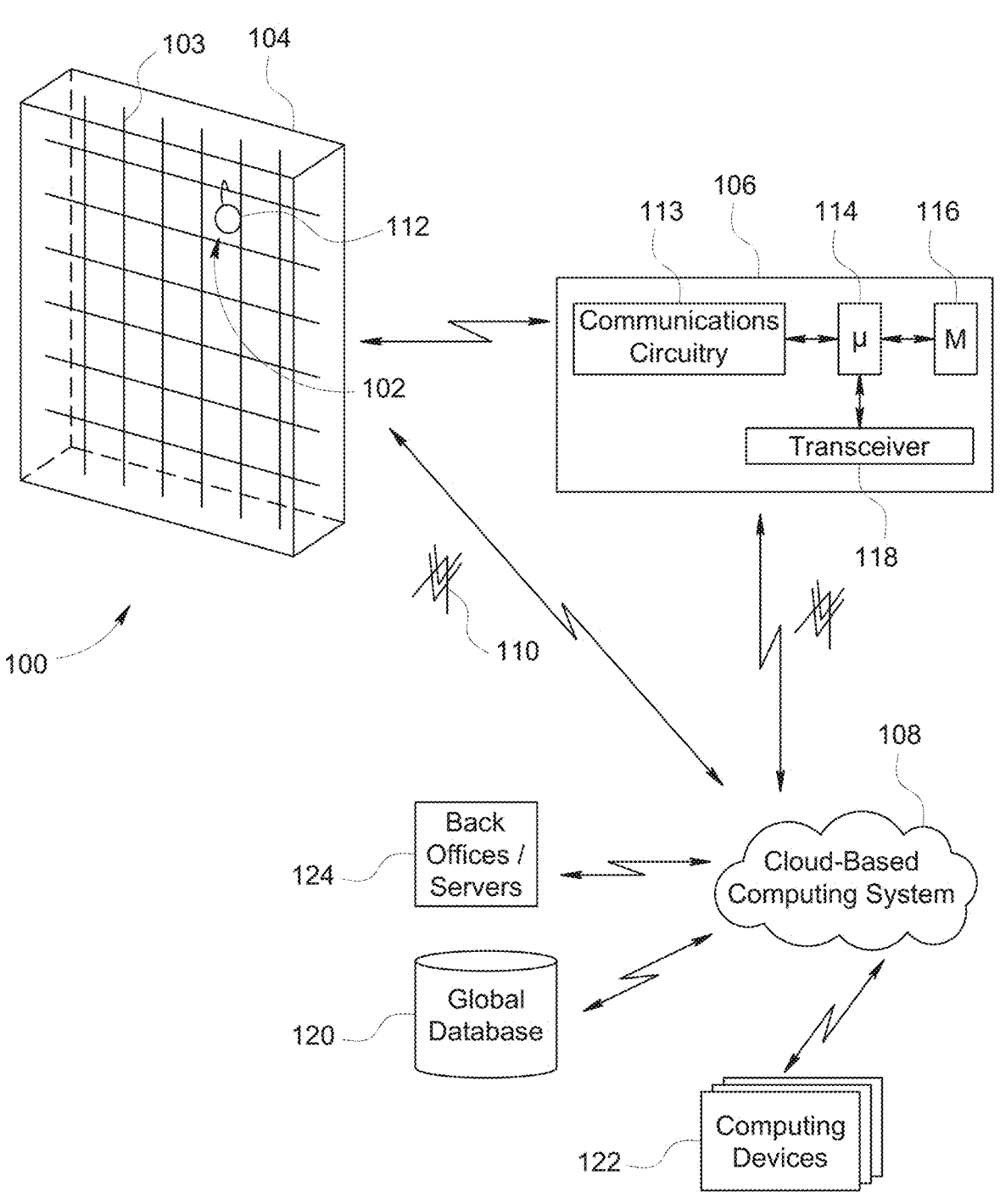
FIG. 1 illustrates an exemplary concrete sensor device embedded into a concrete structure for monitoring one or more properties of the concrete structure and sending the collected data to a remote computing device, in accordance with one or more embodiments.

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

The disclosed embodiments generally relate to a concrete sensor device that can be embedded into a building material (e.g., concrete structure, epoxy, etc.) of a building structure. In certain embodiments, the concrete sensor device monitors properties of the concrete structure, including but not limited to strength, humidity, temperature, vibration, pH, gas and particle presence, load, acoustic properties, or any other physical property that provides an indication of the health of the building material. The concrete sensor device receives information on the one or more properties of the building material and wirelessly transmits the information to a remote computing device (e.g., smartphone, tablet, gateway or other computing device) that is external to the building material. In certain embodiments, the remote computing device may be configured to transmit the information to a cloud-based computing system. In certain embodiments, the concrete sensor may be configured to wirelessly transmit the information to the cloud-based computing system via a cellular transmission and without utilizing any intermediate computing devices.

In certain embodiments, the concrete sensor device is activated prior to installation within the concrete structure. For example, the concrete sensor device may be light activated when an installer removes the concrete sensor device from the light-blocking packaging. As a further example, the concrete sensor device may be activated by a removable streamer, tag, or zip-tie, which when removed by the installer, activates the concrete sensor device. However, it may be beneficial to provide for other methods of sensor activation so that a user may activate the concrete sensor device without manually engaging the sensor device, thereby having greater flexibility during the installation process. Accordingly, it may be beneficial to provide systems and methods for wireless activation of sensor. Specifically, the concrete sensor device includes a power management subcircuit that is configured to turn the concrete sensor "ON" when wirelessly indicated or activated by the remote computing device or by the cloud-based computing system, as further described in detail below with respect to FIGS. 1-4. In certain embodiments, the concrete sensor device includes a capacitor, and the capacitor may be charged by a power source. In particular, when the capacitor is charged by the power source, the power source may send an activation signal to the power management subcircuit.

Turning now to the drawings, FIG. 1 illustrates an exemplary sensor system 100 including a sensor device 102 embedded into a building structure 104 (which, for example, may be a concrete, asphalt, or epoxy structure) for monitoring one or more properties of the building structure and for sending the collected data to a computing device 106 and/or a cloud-based computing system 108, in accordance with aspects of the present disclosure. For illustrative purposes, the building structure 104 will be discussed as a concrete structure and the sensor device 102 will be discussed as a concrete sensor. In certain embodiments, the concrete sensor device 102 is configured to receive wireless activation signals from the computing device 106 and/or the cloud-based computing system 108, in accordance with aspects of the present disclosure.

In certain embodiments, the concrete sensor device 102 is installed within the concrete structure 104 by attaching it to the rebar frame 103 of the concrete structure 104 via an attachment mechanism (e.g., cable tie, zip tie, or any similar mechanism). In certain embodiments, a plurality of concrete sensor devices 102 are attached to a respective plurality of concrete structures 104 within one or more construction sites. The concrete sensor device 102 includes a body 112 (e.g., plastic or rubber body) that encloses one or more components, as further illustrated in FIG. 2. In certain embodiments, after installation and after the concrete is poured, the concrete sensor device includes a sensor opening within the body 112 that allows one or more sensing components (illustrated in FIG. 2) to sense one or more properties of the concrete or other building materials. For example, the concrete sensor device 102 may comprise sensor(s) to monitor one or more properties of the concrete structure 104 such as strength, humidity, temperature, vibration, pH, gas and particle presence, load, acoustic properties, or any other physical property that provides an indication of the health or condition of the concrete structure 104.

Figure 2:
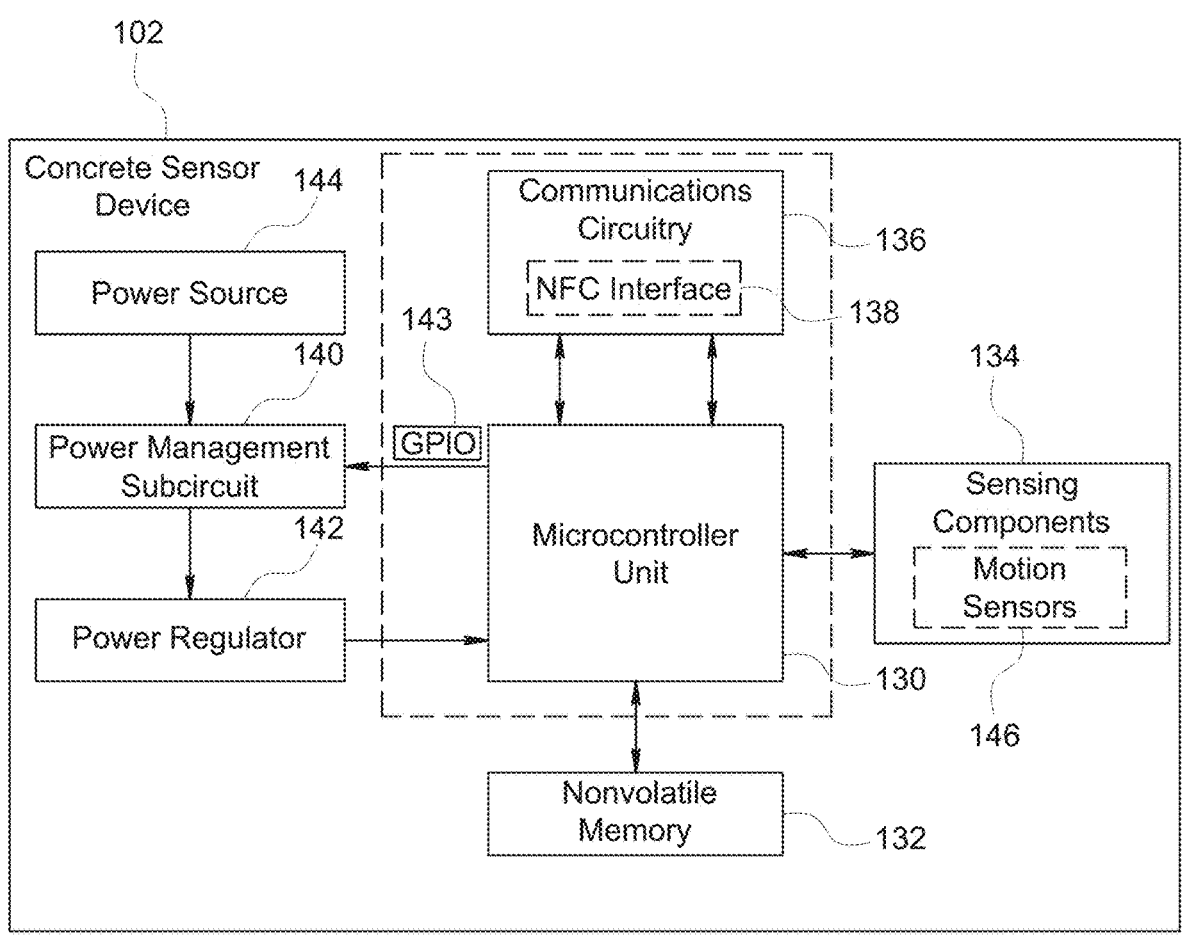
FIG. 2 is a schematic block diagram illustrating certain components of the concrete sensor device of FIG. 1, where the concrete sensor device includes a power management subcircuit, in accordance with one or more embodiments.

In certain embodiments, the concrete sensor device 102 wirelessly transmits the gathered information to the computing device 106 and/or the cloud-based computing system 108 via a radio component (illustrated in FIG. 2). The computing device may include communications circuitry 113 to receive the gathered information from the concrete sensor device. The communications circuitry 113 may include near-field communications circuitry or circuitry that adheres to another type of communications protocol.

In certain embodiments, the computing device 106 is external to the concrete structure 104 and receives information from the concrete sensor device 102 embedded into the concrete structure 104. The computing device 106 may be a handheld device (such as a smartphone, a tablet, a gateway, a personal digital assistant, etc.), a wearable device, or any other computing device that can be utilized on a construction job site to wirelessly communicate with the concrete sensor device 102.

In certain embodiments, the computing device 106 implements one or more operating systems (e.g., Android, Apple iOS, and Windows Phone OS, among others) on which applications run. The operating system(s) allow programmers to create applications or apps to provide functionality to the computing device 106. In certain embodiments, the computing device 106 includes the communications circuitry 113 previously mentioned, a processor (p) 114, a memory (M) 116 readable by the processor 114 for storing applications, instructions, and data, and a transceiver 118. The memory 116 may be a non-transitory computer-readable medium configured to store instructions that are loadable and executable on the processor 114 to perform one or more of the operations described herein. In certain embodiments, the memory 116 may be volatile memory (such as a random access memory (RAM)) and/or non-volatile memory (such as read-only memory (ROM), flash memory, etc.). In some implementations, the memory 132 may include multiple different types of memory, such as static random access memory (SRAM), dynamic random access memory (DRAM), or ROM. The computing device 106 may include various input/output devices, including a display (e.g., touch screen input display) for visual output.

In certain embodiments, the computing device 106 may be configured to transmit information received from the concrete sensor device 102 to the cloud-based computing system 108 via the transceiver 118. Accordingly, in one embodiment a first communications channel may be established between the computing device and sensor device 102 through a first wireless communications (e.g., near-field) channel and the computing device may communicate with the cloud-based computing system 108 over a second wireless communications channel through transceiver 118. While computing system 108 has been described as a cloud-based system, in other embodiments computing system 108 may be different from a cloud-based system. Examples are described below.

In certain embodiments, the cloud-based computing system 108 may be a service provider providing cloud analytics, cloud-based collaboration and workflow systems, distributed computing systems, expert systems and/or knowledge-based systems. In certain embodiments, the cloud-based computing system 108 may be a data repository that is coupled to an internal or external global database 120. Further, in certain embodiments, the global database 120 may allow computing devices 122 to retrieve information stored within for additional processing or analysis. Indeed, the cloud-based computing system may be accessed by a plurality of systems (computing devices 140 and/or computing devices from back offices/servers 124) from any geographic location, including geographic locations remote from the physical locations of the systems. Accordingly, the cloud-based computing system 108 may enable advanced collaboration methods between parties in multiple geographic areas, provide multi-party workflows, data gathering, and data analysis, which may increase the capabilities the concrete sensor device 102.

In certain embodiments, the concrete sensor device 102 may be configured to wirelessly transmit the gathered information (e.g., one or more properties of the concrete structure 104 such as strength, humidity, temperature, vibration, pH, gas and particle presence, load, acoustic properties, or any other physical property that provides an indication of the health or condition of the concrete structure 104) to the cloud-based computing system 108 via a cellular transmission 110 and without utilizing any intermediate computing devices. By utilizing cellular communications, the concrete sensor device 102 may omit various additional devices on the construction site typically used as a gateway, such as a mobile phone, a tablet, the computing device 106 or other processor-enabled devices that act as a gateway. In certain embodiments, the concrete sensor device 102 may be equipped with a wireless communications component (e.g., illustrated in FIG. 2) that enables cellular communications directly with the cloud-based computing system 108. In certain embodiments, other forms of wireless communications may be utilized to transmit information to the cloud-based computing system 108, such as satellite, UHF, VHF, WLANs, Wi-Fi, and so forth.

In particular, in certain embodiments, the concrete sensor device 102 may be wirelessly activated via the computing device 106 or the cloud-based computing system 108 prior to attaching the concrete sensor device 102 to the concrete structure 104. For example, the concrete sensor device 102 may receive one or more wireless activation signals from the computing device 106 of the cloud-based computing system 108, as further described with respect to FIGS. 2-4. In certain embodiments, in response to the received activation signal, the concrete sensor device 102 may power up one or more components of the concrete sensor device 102, thereby turning the concrete sensor device 102 "ON."

FIG. 2 is a schematic block diagram illustrating certain components of the concrete sensor device 102 of FIG. 1, in accordance with one or more embodiments. The concrete sensor device 102 includes a printed circuit board (PCB) assembly. The PCB assembly includes a microcontroller 130, a memory 132, one or more sensing components 134, communications circuitry 136 that may include a near-field communication (NFC) interface 138, a power management subcircuit 140, a power regulator 142, and may be attached to a power source 144 (e.g., a battery or a capacitor).

In certain embodiments, the microcontroller unit 130 may receive information from the one or more sensing components 134, which may include, for example, temperature sensors, humidity sensors, optical sensors, and/or motion sensors 146 (e.g., vibration sensors, position and/or orientation sensors, accelerometers, etc.). In certain embodiments, the one or more sensing components 134 may be disposed inside the sensor body 112 and may sense one or more properties of a building material outside of the sensor body 112 through a sensor opening. A membrane filter may be disposed proximate to the sensor opening to act as a barrier between the components of the concrete sensor device 102 inside the sensor body 112 and the external environment (e.g., liquid water, chemicals, debris of the building material).

In certain embodiments, the microcontroller unit 130 stores the information received from the sensing components 134 within the nonvolatile memory 132. In certain embodiments, the microcontroller unit 130 utilizes the communications circuitry 136 to transmit the gathered information to the computing device 106 and/or the cloud-based computing system 108. The communications circuitry 136 may utilize any wireless communications protocol (e.g., ANT, IEEE 802.11, WiFi, RFID, NFC, Thread, LoRa, ZigBee, etc.) or cellular communication protocols (e.g., high speed packet access [HSPA], HSPA+, long term evolution [LTE], WiMax, near field communications (NFC), Bluetooth, personal area networks (PANs), etc.) to wirelessly communicate information from the concrete sensor device 102 to the computing device 106 and/or the cloud-based computing system 108. In certain embodiments, the concrete sensor 102 may utilize the same wireless and/or cellular communications channels to receive command signals (e.g., activation signals) from the computing device 106 and/or the cloud-based computing system 108, as further described in detail below.

In certain embodiments, the communications circuitry 136 includes an NFC interface 138 that is utilized to receive command signals (e.g., activation signals) from the computing device 106 (e.g., via near-field communications circuitry 113) when brought proximate to or within range of the concrete sensor device 102. As further described with respect to FIG. 3, in certain embodiments, the concrete sensor device 102 may be configured to receive the activation signals via the NFC interface 138, and provide the signal as an input to the power management subcircuit 140. As further described with respect to FIG. 4, in certain embodiments, the concrete sensor device 102 may be configured to receive the activation signals via the communications circuitry 136 from the cloud-based computing system 108, and provide the signal as an input to the power management subcircuit 140. As further described with respect to FIG. 5-6, in certain embodiments, the concrete sensor device 102 may be configured to receive the activation signals via the motion sensors 146, and provide the signal as an input to the power management subcircuit 140.

In certain embodiments, the power management subcircuit 140 includes a PMIC (power management integrated chip) device, a MOSFET, a diode, a momentary tactile button or switch, and supporting passive components (e.g., resistors and capacitors). The PMIC monitors an input connected to the activation button or switch. In certain embodiments, when the PMIC detects an input to the activation button or switch (e.g., the activation button or switch is engaged for a period of time) the output of the power management subcircuit 140 activates the power regulator 142, thereby powering "ON" the microcontroller unit 130 and other device components of the concrete sensor device 102. In certain embodiments, the MOSFET and diode allow the power management subcircuit 140 to soft latch and hold the output logic level in the "active" state. A general purpose input/output (GPIO) 143 from the microcontroller unit 130 may be connected to the power management subcircuit 140 to allow the concrete sensor device 102 to transition back to a "low power mode" during the manufacturing process upon receiving a wireless command.

Figure 3:
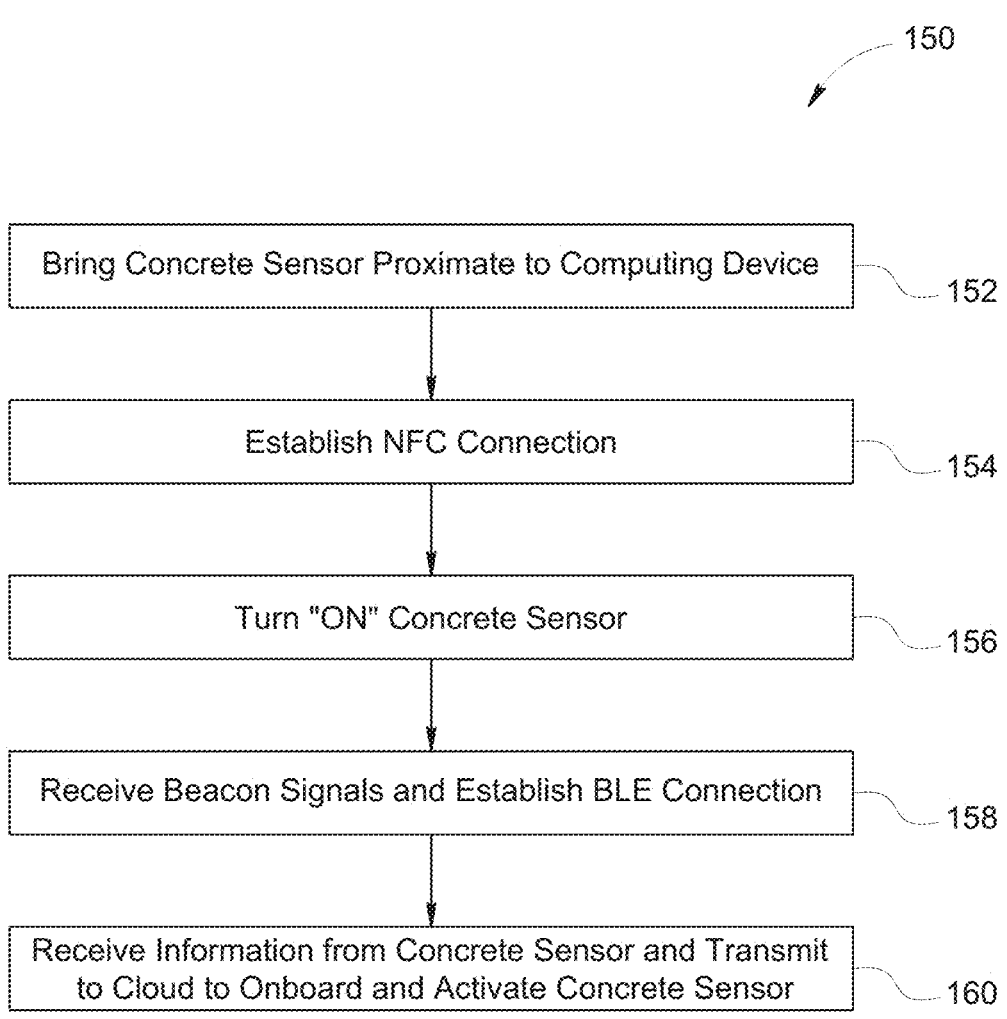
FIG. 3 is a flow diagram illustrating an exemplary process for wirelessly activating the concrete sensor device of FIG. 1 via the remote computing device, in accordance with one or more embodiments.

FIG. 3 is a flow diagram illustrating an exemplary process 150 for wirelessly activating the concrete sensor device 102 of FIG. 1 via the remote computing device 106, in accordance with one or more embodiments. As noted above, it may be beneficial to wirelessly activate the concrete sensor device 102 so that a user may activate the concrete sensor device without manually engaging the concrete sensor device 102, thereby having greater flexibility during the installation process. In certain embodiments, activation of the concrete sensor device 102 includes receiving activation signals to power "ON" the concrete sensor device 102, establishing a wireless communication channel, and onboarding the concrete sensor device 102 to the cloud-based computing system 108, as further described in detail below.

In certain embodiments, the method 150 includes bringing the computing device 106 proximate to the concrete sensor device 102 to bring the NFC interface 138 of the concrete sensor device 102 proximate to or within range of the NFC interface of the computing device 106 (block 152). The method 150 further includes establishing an NFC wireless communication channel between the concrete sensor device 102 and the computing device 106 (block 154).

In certain embodiments, the method 150 further includes transmitting a command signal (e.g., activation signal) from the computing device 106 to the concrete sensor device 102 to turn "ON" the concrete sensor device 102 (block 156). As further described with respect to FIG. 4, the activation signal activates the power management subcircuit 140 to power "ON" the components of the concrete sensor device 102 (block 158). In certain embodiments, upon powering "ON" the concrete sensor device 102, the concrete sensor device 102 emits beacon signals to identify the computing device 106 proximate to the concrete sensor device 102. In certain embodiments, the method 150 further includes receiving the beacon signals from the concrete sensor device 102 via the computing device 106 and establishing a wireless communications channel (e.g., BLE connection or channel) between the computing device 106 and the concrete sensor device 102 (block 158). In certain embodiments, the method further includes the computing device 106 receiving unique identification information of the concrete sensor device 102 and transmitting the received information to cloud-based computing device 108 to onboard the concrete sensor device 102 and activate the concrete sensor device 102 (block 160).

Figure 4:
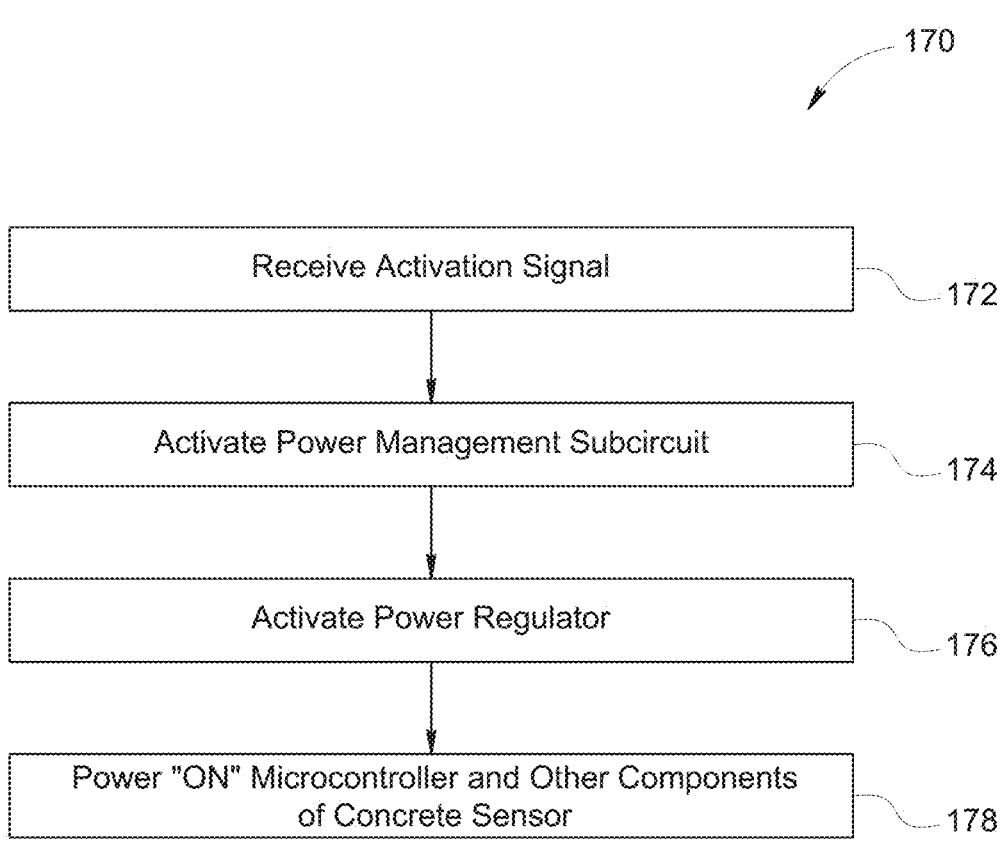
FIG. 4 is a flow diagram illustrating an exemplary process for wirelessly activating the concrete sensor device of FIG. 1 via the power management subcircuit, in accordance with one or more embodiments.

FIG. 4 is a flow diagram illustrating an exemplary process 170 for wirelessly activating the concrete sensor device 102 of FIG. 1 via the power management subcircuit 140, in accordance with one or more embodiments.

In certain embodiments, the concrete sensor device 102 receives a wireless command signal (e.g., activation signal) from the computing device 106 or from the cloud-based computing system 108 (block 172). The activation signal is provided as an input to the power management subcircuit 140 and when the power management subcircuit detects an input, the power management subcircuit is activated (block 174). In certain embodiments, the method further includes the output of the power management subcircuit 140 activating the power regulator 142 (block 176), thereby powering "ON" the microcontroller unit 130 and other device components of the concrete sensor device 102 (block 178).

Figure 5:
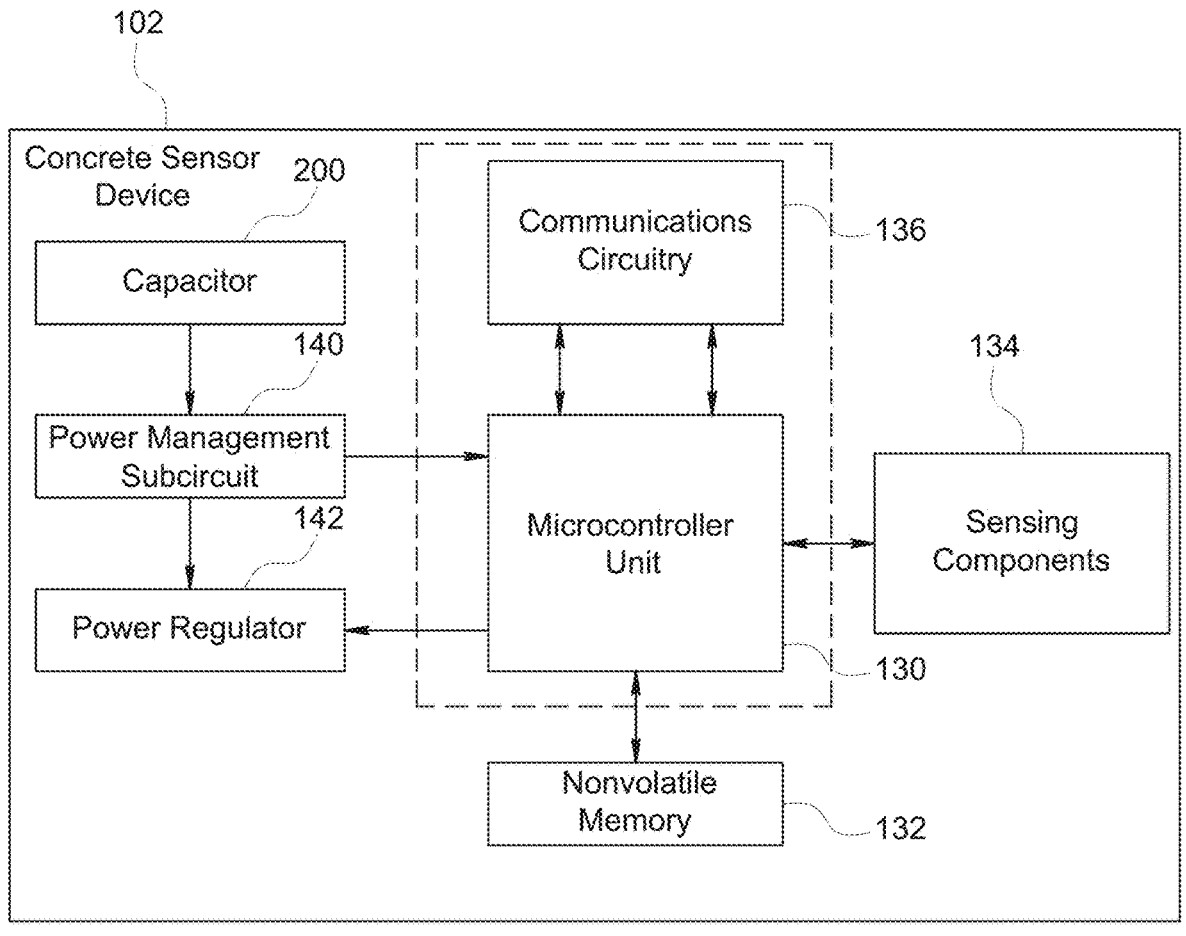
FIG. 5 is a schematic block diagram illustrating certain components of the concrete sensor device of FIG. 1, where the concrete sensor device includes a capacitor, in accordance with one or more embodiments.

FIG. 5 is a schematic block diagram illustrating certain components of the concrete sensor device 102 of FIG. 1, where the concrete sensor device 102 includes a capacitor

200, in accordance with one or more embodiments. The concrete sensor device 102 includes a printed circuit board (PCB) assembly. The PCB assembly includes a microcontroller 130, a memory 132, one or more sensing components 134, communications circuitry 136 that may include an NFC interface 138, a power management subcircuit 140, a power regulator 142, and may be attached to a power source, such as a capacitor 200. In certain embodiments, the capacitor 200 may be utilized as a power source to reduce the overall cost of the concrete sensor device 102. Further, the capacitor 200 may be capable of withstanding higher temperatures within the ambient environment of the building materials.

Figure 6:
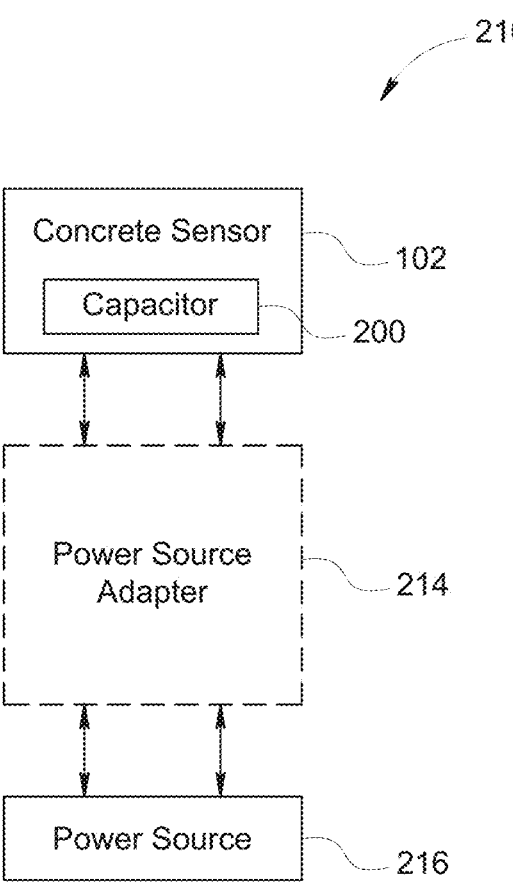
FIG. 6 is a schematic block diagram illustrating an exemplary process for capacitor activation of the concrete sensor device of FIG. 1 with a power source, in accordance with one or more embodiments.

FIG. 6 is a schematic block diagram illustrating a capacitor activation system 210 of the concrete sensor device of FIG. 1 with a power source adapter 214 and a power source 216, in accordance with one or more embodiments. In certain embodiments, the capacitor 200 of the concrete sensor device 102 is charged with a power source 216 that may be typically used for charging power tools or accessories of power tools. In certain embodiments, the power source 216 may be a rechargeable battery pack such as a lithium-ion battery pack of various specifications.

In certain embodiments, the concrete sensor device 102 receives an activation signal from the power source 216 when the concrete sensor device 102 is coupled to the power source 216 via a power source adapter 214 for charging or recharging. In certain embodiments, the concrete sensor device 102 may be directly coupled to the power source 216 for charging or recharging. The activation signal is provided as an input to the power management subcircuit 140 and when the power management subcircuit detects an input, the power management subcircuit is activated (block 174). In certain embodiments, the method further includes the output of the power management subcircuit 140 activating the power regulator 142 (block 176), thereby powering "ON" the microcontroller unit 130 and other device components of the concrete sensor device 102 (block 178).

The methods, processes, and/or operations described herein may be performed by code or instructions to be executed by a computer, processor, controller, or other signal processing device. The computer, processor, controller, or other signal processing device may be those described herein or one in addition to the elements described herein. Because the algorithms that form the basis of the methods (or operations of the computer, processor, controller, or other signal processing device) are described in detail, the code or instructions for implementing the operations of the method embodiments may transform the computer, processor, controller, or other signal processing device into a special-purpose processor for performing the methods herein.

Also, another embodiment may include a computer-readable medium, e.g., a non-transitory computer-readable medium, for storing the code or instructions described above. The computer-readable medium may be a volatile or non-volatile memory or other storage device, which may be removably or fixedly coupled to the computer, processor, controller, or other signal processing device which is to execute the code or instructions for performing one or more operations of the method and apparatus embodiments described herein.

The controllers, processors, regulators, units, components, interfaces, circuits and other signal generating and signal processing features of the embodiments disclosed herein may be implemented, for example, in non-transitory logic that may include hardware, software, or both. When implemented at least partially in hardware, the controllers, processors, regulators, units, components, interfaces, circuits and other signal generating and signal processing features may be, for example, any one of a variety of integrated circuits including but not limited to an application-specific integrated circuit, a field-programmable gate array, a combination of logic gates, a system-on-chip, a microprocessor, or another type of processing or control circuit.

When implemented in at least partially in software, the controllers, processors, regulators, units, components, interfaces, circuits and other signal generating and signal processing features may include, for example, a memory or other storage device for storing code or instructions to be executed, for example, by a computer, processor, microprocessor, controller, or other signal processing device. The computer, processor, microprocessor, controller, or other signal processing device may be those described herein or one in addition to the elements described herein. Because the algorithms that form the basis of the methods (or operations of the computer, processor, microprocessor, controller, or other signal processing device) are described in detail, the code or instructions for implementing the operations of the method embodiments may transform the computer, processor, controller, or other signal processing device into a special-purpose processor for performing the methods described herein.

This written description uses examples to disclose the invention, including the best mode, and also to enable any person skilled in the art to practice the invention, including making and using any devices or systems and performing any incorporated methods. The patentable scope of the invention is defined by the description, and may include other examples that occur to those skilled in the art. Such other examples are intended to be within the scope of the description if they have structural elements that do not differ from the literal language of the description, or if they include equivalent structural elements with insubstantial differences from the literal language of the description. The embodiments may be combined to form additional embodiments.

What is claimed:

1. A system, comprising:
a sensor device configured to monitor one or more properties of a building material within which the sensor device is embedded,
the sensor device comprising a capacitor configured to store electrical energy provided by an external power source, a power management subcircuit having an input electrically coupled to an output of the capacitor and an output electrically coupled to a power regulator,
the power management subcircuit being configured to receive an activation signal from the external power source and, in response to the activation signal, to control discharge of the capacitor to the power regulator,
the power regulator having an input electrically coupled to the output of the power management subcircuit and an output electrically coupled to a microcontroller unit, the power regulator being configured to provide regulated electrical power to the microcontroller unit,
the microcontroller unit having a power input electrically coupled to the output of the power regulator,
a first interface electrically coupled to one or more sensing components configured to measure the one or more properties of the building material,
a second interface electrically coupled to a nonvolatile memory configured to store data representing the one or more properties of the building material as measured by the sensing components, and
a third interface electrically coupled to communications circuitry configured to wirelessly transmit data representing the one or more properties to a computing device external to the building material,
wherein, in response to the activation signal, the power management subcircuit is configured to discharge the capacitor to the power regulator.

2. The system of claim 1, wherein the power management subcircuit comprises an activation switch that is triggered by the activation signal.

3. The system of claim 1, wherein the external power source is a battery pack.

4. The system of claim 1, wherein the controller microcontroller unit is configured to receive data regarding the one or more properties of the building material from the one or more sensing components after the sensor device is activated and embedded into the building material.

5. The system of claim 4, wherein the microcontroller unit is configured to wirelessly transmit the data regarding the one or more properties of the building material to the computing device external to the building material using one or more wireless or cellular communication protocols.

6. The system of claim 1, wherein the computing device is a smartphone, a personal computer, a tablet, a gateway, a wearable computer, or a personal digital assistant.

7. The system of claim 1, wherein the building material comprises concrete, asphalt, or epoxy.

8. The system of claim 1, wherein the one or more properties comprise building material strength, relative humidity, temperature, vibration, pH, gas and particle presence, load, and/or acoustic properties.

* * * * *